United States Patent
Rice et al.

(10) Patent No.: US 8,089,632 B2
(45) Date of Patent: Jan. 3, 2012

(54) SYSTEMS AND METHODS FOR DETECTING CONTAMINANTS

(75) Inventors: Robert Rex Rice, Simi Valley, CA (US); William Byron Cottingame, Newbury Park, CA (US)

(73) Assignee: Northrop Grumman Systems Corporation, Los Angeles, CA (US)

( * ) Notice: Subject to any disclaimer, the term of this patent is extended or adjusted under 35 U.S.C. 154(b) by 877 days.

(21) Appl. No.: 12/135,626

(22) Filed: Jun. 9, 2008

(65) Prior Publication Data
US 2011/0290026 A1    Dec. 1, 2011

(51) Int. Cl.
*G01B 9/02*  (2006.01)
(52) U.S. Cl. ........................................ 356/502
(58) Field of Classification Search .................. 356/237, 356/502
See application file for complete search history.

(56) References Cited

U.S. PATENT DOCUMENTS

| | | | | |
|---|---|---|---|---|
| 5,748,317 A | * | 5/1998 | Maris et al. | 356/502 |
| 5,926,273 A | * | 7/1999 | Kimura et al. | 356/502 |
| 6,320,665 B1 | | 11/2001 | Ngoi et al. | |
| 6,628,404 B1 | * | 9/2003 | Kelley et al. | 356/502 |
| 6,728,645 B1 | | 4/2004 | Kozlov et al. | |
| 6,943,884 B2 | | 9/2005 | Rice | |
| 7,089,796 B2 | | 8/2006 | Pepper et al. | |
| 2005/0207943 A1 | | 9/2005 | Puzey | |
| 2007/0091316 A1 | | 4/2007 | Lal et al. | |

* cited by examiner

*Primary Examiner* — Hwa Lee
(74) *Attorney, Agent, or Firm* — Tarolli, Sundheim, Covell & Tummino LLP

(57) ABSTRACT

Systems and methods are provided for detecting contaminants associated with a target. In one embodiment, a system is provided that comprises a tunable laser configured to transmit an illuminator pulse at a target for a predetermined time duration and a laser Doppler vibrometer system configured to transmit a probe pulse at a surface of the target within the predetermined time duration. The laser Doppler vibrometer system is further configured to detect and analyze at least one return pulse of the probe pulse to determine a surface expansion velocity of contaminants associated with the target due to the illuminator pulse.

20 Claims, 5 Drawing Sheets

SYSTEMS AND METHODS FOR DETECTING CONTAMINANTS

TECHNICAL FIELD

The present invention relates generally to detection systems, and more particularly to systems and methods for detecting contaminants.

BACKGROUND

Many image systems exist that employ local or remote non-destructive sensing of spectrally dependent properties of substances for identifying the presence of one or more substances. These substances could include, for example, gases, chemicals, minerals, pollutants, and objects both man-made and natural in the form of a gas, liquid or solid. Examples of local sensing and identifying methods that have been used to detect spectral properties include ion mobility spectrometry, flame photometry, mass spectrometry, electrochemistry, detection paper methods, surface acoustic wave methods, laser-induced breakdown spectroscopy, photo ionization detection, gas chromatography and cavity-ring-down spectroscopy. Local sensing and identifying systems and methods are limited by the ability to retrieve a sample or locate detection equipment near a target area.

Furthermore, it is often desirable to know from a distance the presence of dangerous agents, substances or devices near a target area. For example, in modern warfare, explosives, such as individual improvised explosive devices or entire weapon manufacturing sites, leave a chemical residue and/or chemical plume. It is generally unknown what chemical agents are present in the chemical residue and/or chemical plume and what type of target may be hidden behind the target surface. It is also desirable to know from a distance what agents might be present due to a chemical fire or spill. Though these are merely exemplary, it is understood that it is generally desirable to know the agents and substances in contaminates associated with a remote target or region before any individual comes in contact with or in close proximity to the remote target or region.

SUMMARY

In one aspect of the invention, a system is provided for detecting contaminants associated with a target. The system comprises a tunable laser configured to transmit an illuminator pulse at a target for a predetermined time duration and a laser Doppler vibrometer system configured to transmit a probe pulse at a surface of the target within the predetermined time duration. The probe pulse is further configured to detect and analyze at least one return pulse of the probe pulse to determine a surface expansion velocity of contaminants associated with the target due to the illuminator pulse.

In another aspect of the invention, a system is provided for detecting contaminants associated with a target. The system comprises means for transmitting an illuminator pulse at a target for a predetermined time duration, means for transmitting a doublet pulse at a surface of the target within the predetermined time duration and means for detecting return signals of the doublet pulse. The system further comprises means for determining a surface expansion velocity of contaminants associated with the target due to the illuminator pulse.

In yet another aspect of the invention, a method is provided for detecting contaminants associated with a target. The method comprises transmitting an illuminator pulse of a given wavelength at a target for a predetermined time duration, transmitting a Doppler vibrometry doublet pulse during the predetermined time duration and determining a phase difference between the return pulses of the transmitted Doppler vibrometry doublet pulse. The methodology further comprises determining a surface expansion velocity of a contaminant associated with the target based on the determined phase difference.

DETAILED DESCRIPTION

Figure 1:
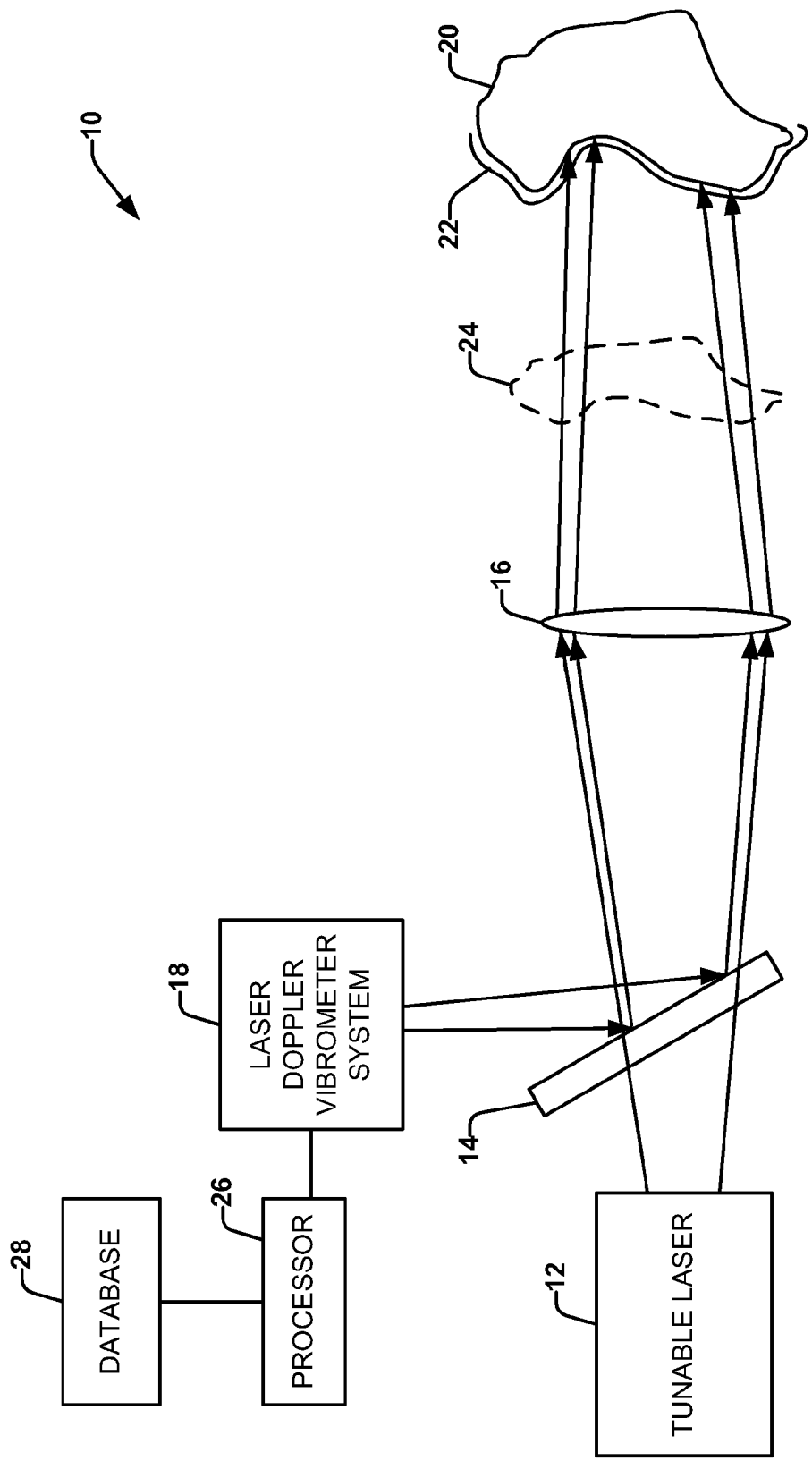
FIG. 1 illustrates a block schematic diagram of a system for detecting contaminants associated with a target in accordance with an aspect of the present invention.

Systems and methods for detecting contaminants associated with targets are disclosed. For example, dangerous targets such as improvised explosive devices give off a chemical residue (e.g., gas, liquid or powder) and/or gaseous cloud in the form of a chemical plume. The targets may be hidden from image systems but the contaminants can be detected and employed to identify the existence of a dangerous target. Additionally, some targets may generate pollutants that cannot be detected by visual image systems. These contaminants can be detected and employed to identify the existence of an environmentally unfriendly device, machine, vehicle or building. It is to be appreciated that the systems and method can be employed to detect a variety of chemical contaminants associated with respective targets. A target can be a variety of different structures residing in a target area, such as a weapon, vehicle, building, a person, an animal, a liquid, a gas, or a solid reflective surface that give off a chemical residue and/or chemical plume. A contaminant can be formed of one or more chemical compounds associated with a target.

In one aspect of the invention, a tunable laser is configured to transmit an illuminator pulse at a target for a predetermined time duration. The illuminator pulse causes the surface of the contaminants associated with the target to heat and expand. A laser Doppler vibrometer system transmits a probe pulse (e.g., a doublet pulse, continuous wave pulse) at the target within the predetermined time duration and detects and analyzes the return signal(s) of the probe pulse. The return signals can be employed to determine the distance moved by a surface of contaminants associated with the target. The distance moved can be employed to determine the surface expansion velocity of the contaminant. For example, the phase difference between the optical carriers of doublet pulses is proportional to the distance moved by the contaminant surface. The surface expansion velocity is proportional to the phase shift difference divided by the pulse interval. The surface expansion velocity depends on the laser energy absorbed and the thermal expansion coefficient of the contaminant type.

In one aspect of the invention, a tunable laser sequentially transmits illuminator pulses over a plurality of wavelengths to induce surface expansion of contaminants associated with a target. The laser Doppler vibrometer system is configured to determine a plurality of corresponding surface expansion velocities associated with the plurality of illuminator pulses at the different wavelengths and analyze a spectral pattern shape signature of the plurality of the surface expansion velocities to determine a type of contaminant associated with the target. The spectral pattern shape signature can be determined by comparing ratios of the surface expansion velocities at the different wavelengths. The different wavelengths can be selected to select one or more wavelengths for which the contaminant surface is strongly absorbing and one or more wavelengths for which the contaminant surface is not strongly absorbing. The difference in induced velocity between strongly absorbing wavelengths and weakly absorbing wavelengths can provide a differential absorption measurement that can be employed to determine a type of contaminant. The type of contaminant can be employed to determine the type of target.

Although the present examples will be illustrated with respect to transmitting a laser Doppler vibrometer doublet probe pulse, it is to be appreciated that the present invention can employ a continuous wave probe pulse can be employed to carry out the present invention. It is also appreciated that the present invention can be employed to determine if a specific contaminant(s) is or is not present by adjusting the illuminator pulse wavelengths to search for specific materials.

FIG. 1 illustrates a schematic block diagram of a system 10 for detecting contaminants associated with a target in accordance with an aspect of the present invention. The system 10 includes a tunable laser 12 configured to transmit an illuminator pulse at a surface of a target 20 and a laser Doppler vibrometer 18 configured to measure the surface expansion velocity of a contaminant associated with the target 20. The contaminant can be a surface contaminant 22 and/or a chemical plume 24 associated with the target 20. The tunable laser 12 is tunable to transmit laser illuminator pulses over a plurality of wavelengths. When the wavelength of the illuminator pulse coincides with an absorption band of the contaminant 22 and/or contaminant 24 associated with the target 20, the surface expansion velocity of the contaminant will increase due to an increase in energy absorbed by the contaminant. Therefore, to determine a spectral pattern shape signature of a contaminant associated with the target 20, the tunable laser 12 can be tuned to sequentially transmit light over a plurality of wavelengths and the laser Doppler vibrometer system 18 can be configured to determine a surface expansion velocity at each of the plurality of wavelengths.

The system 10 further comprises a beam combiner 14 (e.g., dichroic beam splitter) and a telescope lens 16. The lens 14 focuses the light beams from the tunable laser 12 and the laser Doppler vibrometer system 18 onto the surface of the target 20. The beam combiner 16 is configured to allow a doublet pulse from the laser Doppler vibrometer system 18 to be transmitted concurrently with the illuminator pulse. The doublet pulse can be set at a wavelength that has a narrow line width (e.g., 1 micron). The tunable laser 12 can be configured to sequentially transmit illuminator pulses at a surface of a target 20 over a set of target wavelengths of interest, for example, in the mid-wave infrared (MWIR) range. The target wavelengths can be selected to correspond to absorption features of particular chemical residue and/or plumes having high gain spectral features at certain wavelengths and low gain spectral features at certain wavelengths, such that a spectral pattern shape signature can be employed to identify contaminants associated with a target 20. In one aspect of the invention, a plurality of discrete wavelength bands are scanned to avoid wavelengths of the atmospheric absorption spectra, thus reducing power employed to perform the scan.

The laser Doppler vibrometer system 18 detects the vibrational response caused by the illuminator pulse being absorbed by the target 20. The laser Doppler vibrometer system 18 receives the doublet pulses reflected back from the contaminants (e.g., chemical residue 22, chemical plume 24) associated with the target 20, wherein the reflected pulses are frequency shifted proportionally to the absorption of the light from the tunable laser 12. Because the absorption of light from the tunable laser 12 is also proportional to the surface deformation of the contaminants associated with the target 20, each reflected pulse is indicative of the position of the contaminant surface at the time the pulse was sent. Therefore, the synchronized doublet pulse can be employed to measure the velocity of the surface deformation of the contaminant by determining the phase difference between the optical carriers of doublet pulses divided by the pulse interval. Preferentially absorbed frequencies will be detected as spikes in the velocity of surface deformation by the laser Doppler vibrometer system 18. The response should be substantially uniform for wavelengths that are not preferentially absorbed.

The system 10 can further comprise a processor 26 and a database 28. The database 28 can store known surface expansion velocity data for a plurality of substances in the form of spectral pattern shape signatures. The processor 26 can analyze and determine ratios between captured surface expansion velocity data for different wavelengths to determine a spectral pattern shape signature. The processor 26 then determines whether the sample spectral pattern shape signature substantially matches any of the stored known spectral pattern shape signature. In one aspect of the invention, the system can be employed as a system for detecting and discerning between multiple chemicals in a contaminant either or both in the form of chemical residue and/or chemical plumes.

The tunable laser 12 can be, for example, an optical parametric oscillator (OPO) or other tunable laser that can provide wavelengths in the mid-wave infrared range. The system 10 can be used at distance of miles from the target 20. However, the atmosphere may obstruct some wavelengths from transmitting. To compensate, the tunable laser 12 may employ wavelength transmission windows at which the atmosphere does transmit well and detect spectral features at those wavelengths. In one aspect of the invention, the laser Doppler vibrometer system 18 may employ a continuous wave (CW) approach with a continuous probe beam at a fixed wavelength that illuminates the surface of the target 20 so the response of contaminants associated with the target produces frequency modulation that is coherently detected. The reflected probe beam can be employed to determine surface expansion velocity of contaminants associated with the target 20.

Figure 2:
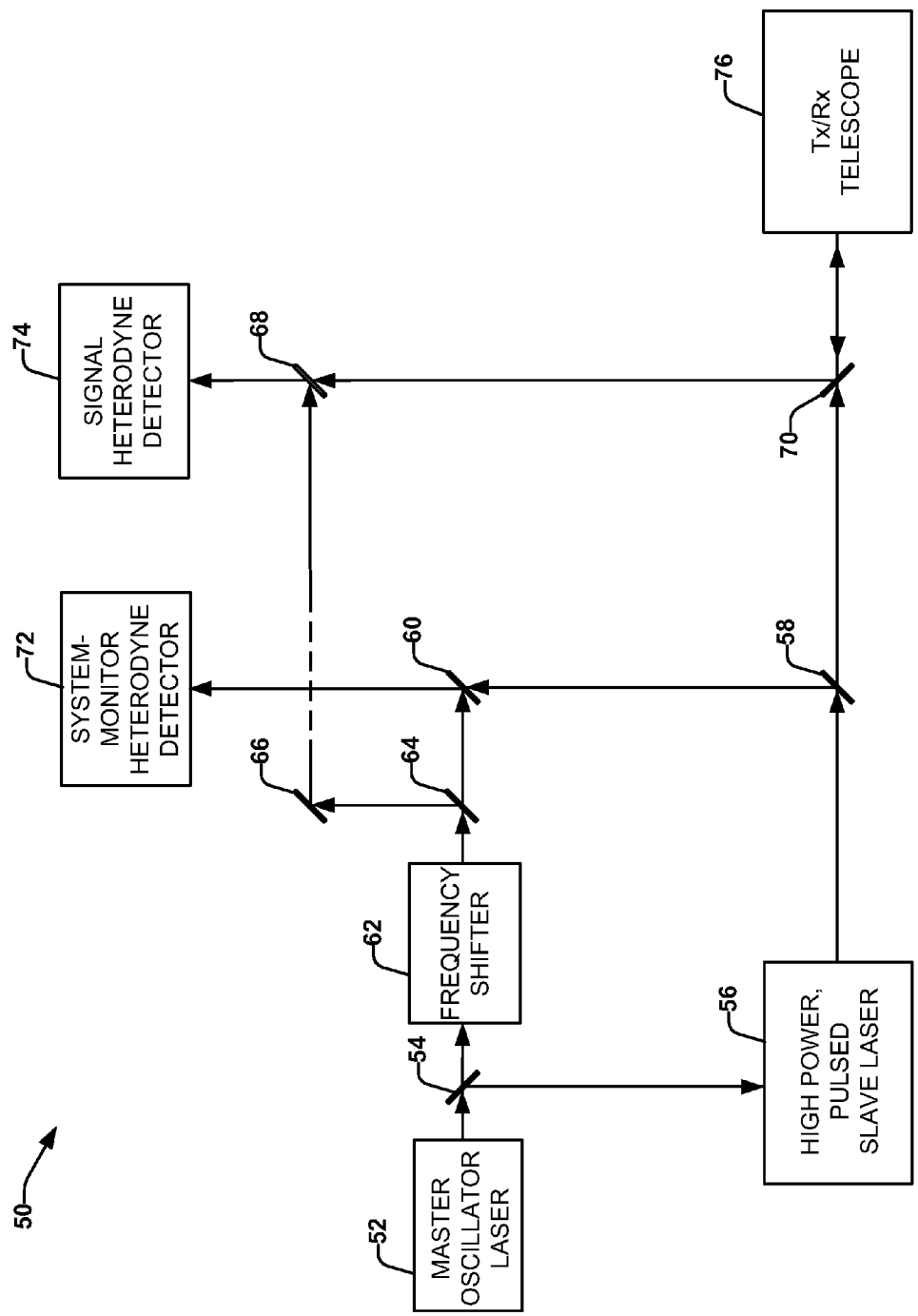
FIG. 2 illustrates a block schematic diagram of the laser Doppler vibrometer system in accordance with an aspect of the present invention.

FIG. 2 illustrates a schematic block diagram of a doublet pulse vibrometer system 50 in accordance with an aspect of the present invention. The laser Doppler vibrometer system 50 employs a master oscillator 52 that acts as a frequency stable source. A beam splitter 54 directs a portion of that signal to a high power pulsed slave laser 56, allowing the slave laser 56 to phase lock with the master oscillator 52. The slave laser 56 emits a pair of sequential short amplitude modulated pulses on an optical carrier, each lasting anywhere from about ten nanoseconds to about one hundred nanoseconds. The pulses are directed to a transmitting-receiving telescope 76. A beam splitter 58 diverts a portion of the slave laser 56 pulses to a system monitor heterodyne detector 72. The system monitor heterodyne detector 72 detects the difference between the outgoing pulses of the slave laser 56 and the master oscillator 52 and determines and corrects for any error to essentially phase lock the slave laser 56 with the master oscillator 52.

The transmitting-receiving telescope 76 receives return pulses from the contaminants associated with a target. The beam splitter 70 directs the return pulses to a signal heterodyne detector 74. The signal heterodyne detector 74 also receives a signal from the master oscillator 52 through frequency shifter 62, beam splitter 64, beam splitter 66, and beam splitter 68. Each return pulse received from the transmitting-receiving telescope 76 is superimposed on the signal from the master oscillator 52 to measure the instantaneous phase shift of the return pulse for both pulses of the doublet pulse. The phase difference between the optical carriers of the doublet pulses is proportional to the distance moved by the contaminant surface associated with a target that is being illuminated, which is further proportional to the surface expansion velocity of the contaminant.

Figure 3:
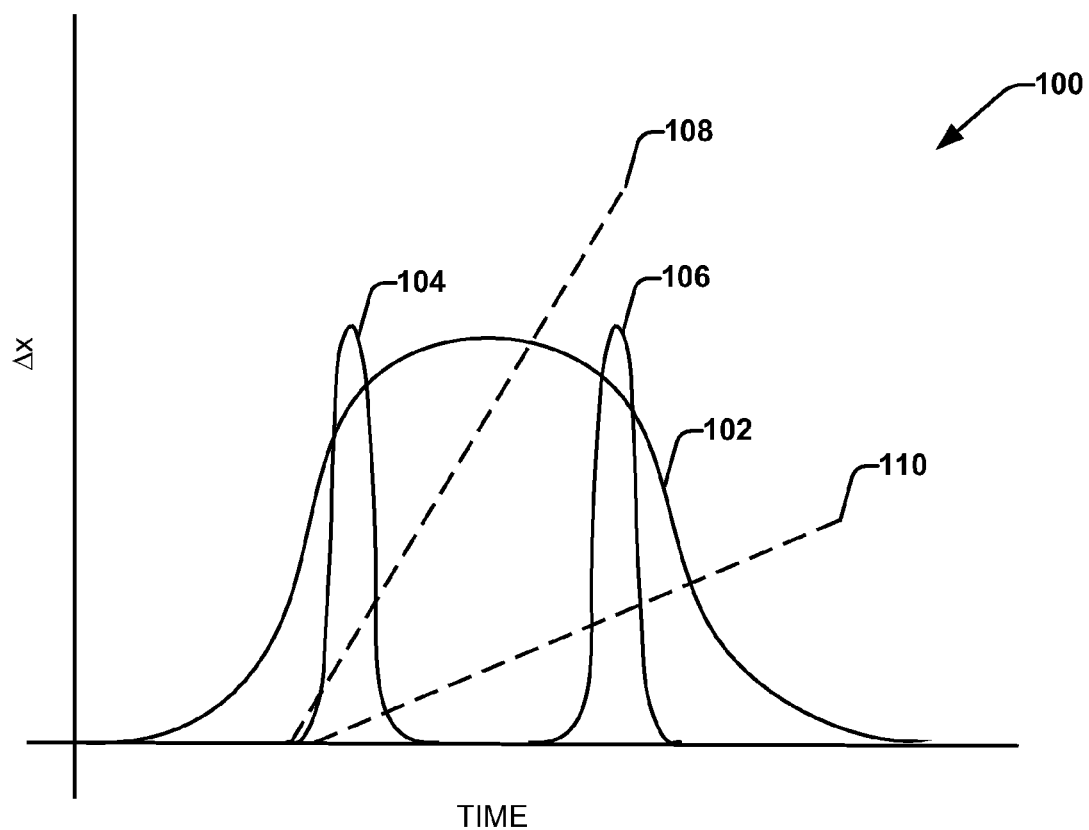
FIG. 3 illustrates a graph of displacement versus time of a surface of a contaminant associated with a target in accordance with an aspect of the present invention.

FIG. 3 illustrates a graph 200 of displacement versus time of a surface of a contaminant associated with a target in accordance with an aspect of the present invention. The graph 100 further illustrates the employment of a doublet pulse vibrometer technique to detect displacement of the surface of the contaminant in response to an illuminator pulse 102. The illuminator pulse 102 is incident on surface of a target for a predetermined time duration, such as about one hundred nanoseconds. The laser Doppler vibrometer system transmits the doublet pulses 104 and 106 during the predetermined time duration.

The return pulses of the doublet pulses 104 and 106 are employed to measure the near adiabatic deformation of the contaminant surface associated with a target. Doublet pulses 104 and 106 measure the surface position by detecting the phase shift difference in the return pulses of the doublet pulses 104 and 106. For example, doublet pulse 104 is transmitted to the surface, and the phase shift in the return pulse is proportional to the energy absorbed from the illuminator pulse 102 and thus is proportional to the deformation of the contaminant surface. This measurement is performed again with the doublet pulse 106. The measurements of the deformation of the contaminant surface are employed to determine surface expansion velocity during absorption of the illuminator pulse 102. The doublet pulses 104 and 106 can be at a reduced frequency relative to the illuminator pulse 102, so as not to cause any additional heating of the surface, and can be of narrow line width, such that the sensitivity is facilitated.

When the illuminator pulse 102 is preferentially absorbed by the contaminant surface, the surface deformation will occur rapidly and a slope of the plotted surface deformation will be relatively steep as illustrated in a first displacement response 108 resulting in graphically defined spectral features. Conversely, if the contaminant surface does not preferentially absorb illuminator pulse 102, the plotted surface deformation 108 will have a relatively gradual slope as illustrated in a second displacement response 110. A spectral pattern shape signature can be determined by comparing the surface deformation and analyzing ratios of surface expansion velocity at wavelengths of preferential absorption and wavelengths that do not preferentially absorb, for example, by employing fitting algorithms. The contaminants can be identified by comparing the determined spectral pattern shape signature against known spectral pattern shape signatures, for example, by employing fitting algorithms.

Figure 4:
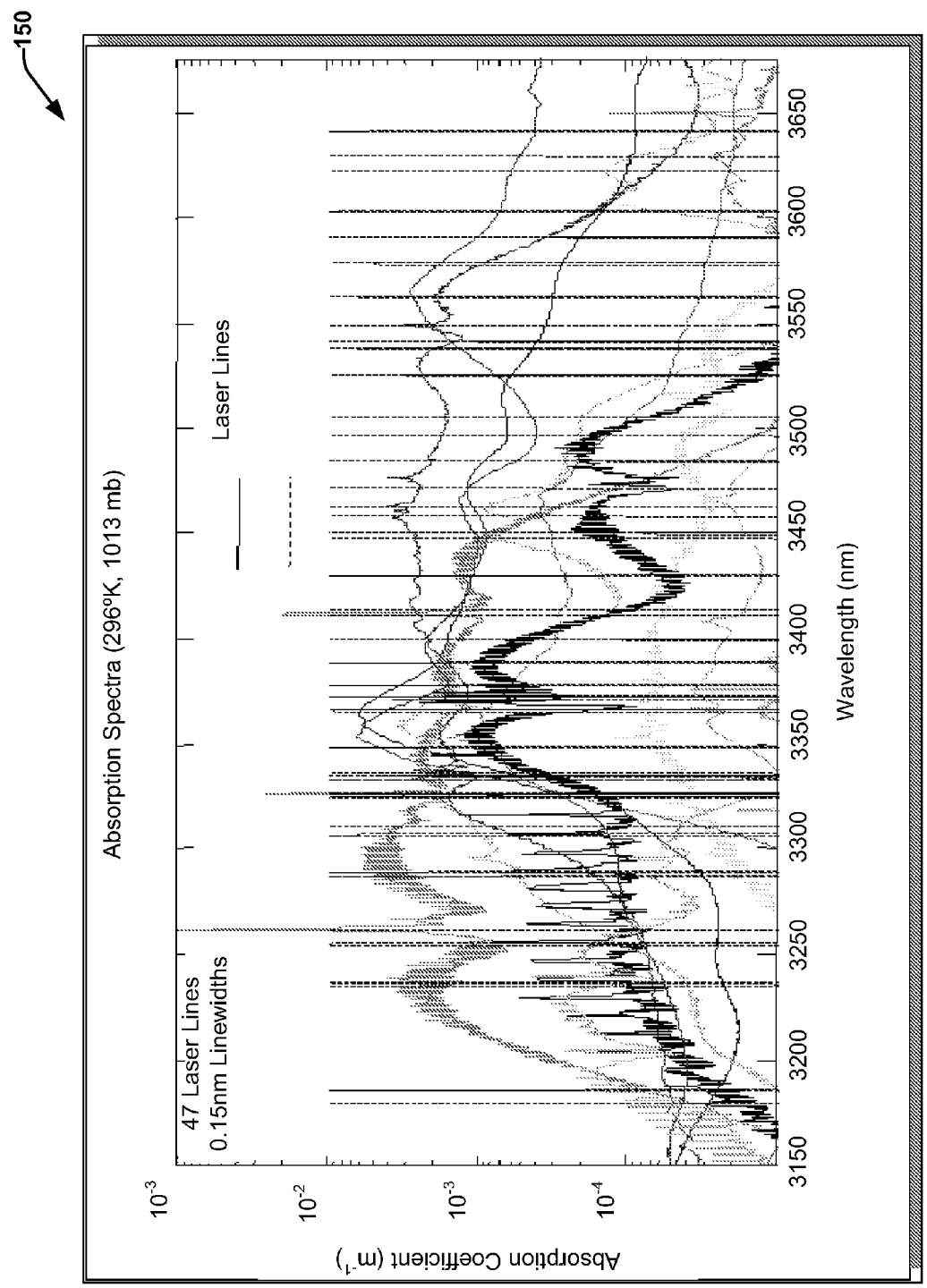
FIG. 4 illustrates an absorption spectra graph that can be employed to evaluate spectral feature signatures for a plurality of different contaminants in accordance with an aspect of the present invention.

FIG. 4 illustrates an absorption spectra graph 150 that can be employed to evaluate spectral pattern shape signatures for a plurality of different contaminants in accordance with an aspect of the present invention. The graph 150 also illustrates wavelengths where the absorption coefficient of the atmosphere is relatively high, as indicated by the vertical dash lines. The system 10 can be configured to scan discrete wavelength bands to avoid the wavelengths in which the absorption coefficient of the atmosphere is relatively high. In this manner, power consumed and scan time of the system 10 can be reduced. The graph 150 can be employed to determine spectral pattern shape signatures by storing signatures at wavelengths where absorption values and surface deformation velocities are obtained for a given contaminant type over a set of wavelengths that provide both peak, median and minimum values to determine a given pattern shape. The spectral pattern shape signatures can be stored in a database for comparing to sample spectral pattern shape signatures to determine contaminant types associated with the target 20. Additionally, the system 10 can be configured to scan certain wavelengths to look for contaminant types associated with a target based on the predetermined spectral pattern shape signatures.

Figure 5:
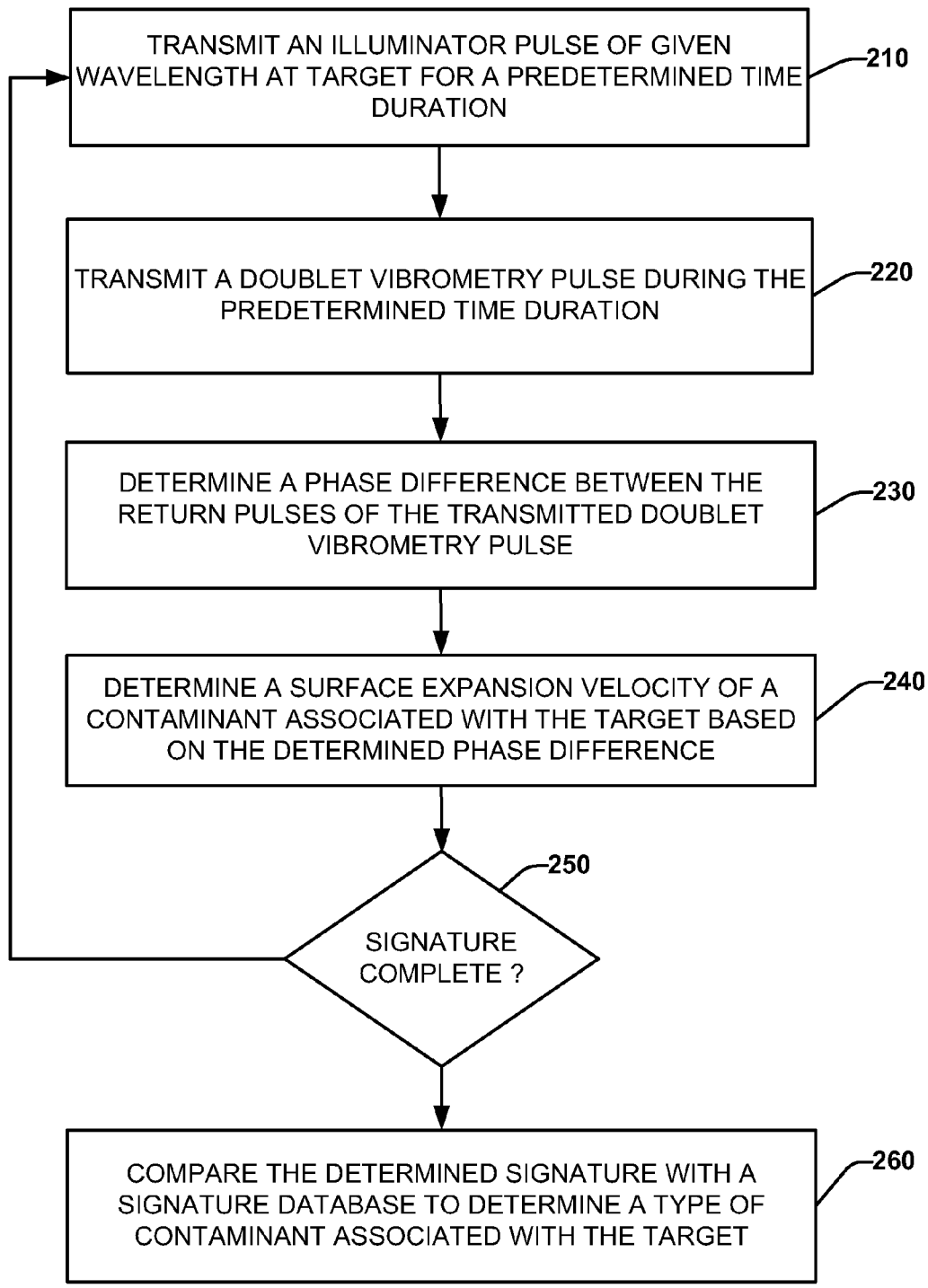
FIG. 5 illustrates a methodology for detecting contaminants associated with a target in accordance with an aspect of the present invention.

FIG. 5 illustrates a methodology for detecting contaminants associated with targets in accordance with an aspect of the present invention. The methodology begins at 210 where an illuminator pulse of a given wavelength is transmitted at a target for a predetermined time duration. At 220, a Doppler vibrometry doublet pulse is transmitted during the predetermined time duration. At 230, a phase difference between the return pulses of the transmitted Doppler vibrometry doublet pulse is determined. At 240, a surface expansion velocity of a contaminant associated with the target is determined based on the determined phase difference divided by the pulse interval. The methodology then proceeds to 250. At 250, it is determined if the last wavelength has been transmitted of a plurality of selected given wavelengths. If the last wavelength has not been transmitted (NO), the methodology returns to 210 to repeat 210-240 at a next given wavelength. The wavelengths can be selected to search for specific contaminant types or to scan wavelengths in the available atmospheric windows to search for a large number of potential contaminant candidates. If the last wavelength has been transmitted (YES), the methodology proceeds to 260. At 260, the ratios of the determined surface expansion velocities are compared to determine a spectral pattern shape signature. At 270, the determined spectral pattern shape signature is compared with one or more predetermined spectral pattern shape signatures to determine a presence of a contaminant associated with a target.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the scope of the appended claims.

What is claimed is:

1. A system for detecting contaminants associated with a target, the system comprising:
   a tunable laser configured to transmit an illuminator pulse at a target for a predetermined time duration; and
   a laser Doppler vibrometer system configured to transmit a probe pulse at a surface of the target within the predetermined time duration and detect and analyze at least one return pulse of the probe pulse to determine a surface expansion velocity of contaminants associated with the target due to the illuminator pulse.

2. The system of claim 1, wherein the tunable laser is configured to transmit a plurality of illuminator pulses over a plurality of wavelengths and the laser Doppler vibrometer system is configured to determine a plurality of corresponding surface expansion velocities associated with the plurality of illuminator pulses.

3. The system of claim 2, further comprising a signal processor that calculates a surface expansion velocity based on a phase shift between return pulses of the illuminator pulse for each of the plurality of wavelengths and analyzes the plurality of the surface expansion velocities to determine a spectral pattern shape signature.

4. The system of claim 3, wherein the signal processor compares the determined spectral pattern shape signature to one or more predetermined spectral pattern shape signatures to determine a type of contaminant associated with the target.

5. The system of claim 1, wherein the tunable laser operates in the mid-wave infrared range.

6. The system of claim 5, wherein the tunable laser is configured to scan discrete wavelength bands to avoid the wavelengths in which the absorption coefficient of the atmosphere is relatively high.

7. The system of claim 1, wherein the contaminant is a chemical plume between the target and the system.

8. The system of claim 1, wherein the contaminant resides on the surface of the target.

9. The system of claim 1, wherein the probe pulse is a doublet pulse.

10. The system of claim 1, wherein the Doppler vibrometer system comprises a heterodyne detector to measure a phase shift difference of the doublet pulse.

11. A system for detecting contaminants associated with a target, the system comprising:
    means for transmitting an illuminator pulse at a target for a predetermined time duration;
    means for transmitting a doublet pulse at a surface of the target within the predetermined time duration;
    means for detecting return signals of the doublet pulse; and
    means for determining a surface expansion velocity of contaminants associated with the target due to the illuminator pulse.

12. The system of claim 11, wherein the means for transmitting an illuminator pulse is configured to transmit a plurality of illuminator pulses over a plurality of wavelengths, the means for transmitting a doublet pulse is configured to transmit a respective doublet pulse within the predetermined time duration of each of the plurality of illuminator pulses and the means for determining a surface expansion velocity is configured to determine a spectral pattern shape signature based on determined and compared surface expansion velocities for each of the plurality of illuminator pulse wavelengths.

13. The system of claim 12, further comprising means for comparing a determined spectral pattern shape signature with one or more spectral pattern shape signatures to determine a type of contaminant associated with the target.

14. The system of claim 12, wherein the plurality of wavelengths comprise wavelengths in the mid-wave infrared range.

15. The system of claim 14, wherein the means for transmitting an illuminator pulse is configured to scan discrete wavelength bands to avoid the wavelengths in which the absorption coefficient of the atmosphere is relatively high.

16. A method for detecting contaminants associated with a target, the method comprising:
    transmitting an illuminator pulse of a given wavelength at a target for a predetermined time duration;
    transmitting a Doppler vibrometry doublet pulse during the predetermined time duration;
    determining a phase difference between the return pulses of the transmitted Doppler vibrometry doublet pulse; and
    determine a surface expansion velocity of a contaminant associated with the target based on the determined phase difference.

17. The method of claim 16, further comprising transmitting a plurality of illuminator pulses over a plurality of wavelengths, transmitting respective Doppler vibrometry doublet pulses within the predetermined time duration of each of the plurality of illuminator pulses and determining a plurality of corresponding surface expansion velocities associated with the plurality of illuminator pulses, comparing the plurality of corresponding surface expansion velocities to determine a spectral pattern shape signature.

18. The method of claim 17, further comprising comparing the determined spectral pattern shape signature to one of more predetermined spectral pattern shape signatures to determine a type of contaminant associated with the target.

19. The method of claim 17, wherein the plurality of wavelengths comprises discrete wavelength bands that avoid the wavelengths in which the absorption coefficient of the atmosphere is relatively high.

20. The method of claim 16, wherein the contaminant resides on the surface of the target and/or is a chemical plume spaced apart from the target.

* * * * *